United States Patent [19]

Tranner

[11] Patent Number: 5,508,024

[45] Date of Patent: Apr. 16, 1996

[54] TOPICAL ANTIPERSPIRANT COMPOSITION CONSISTING ESSENTIALLY OF NON-TOXIC WATER-INSOLUBLE OCCLUSIVE FILM-FORMING ANTIPERSPIRANT POLYMER

[75] Inventor: Frank Tranner, Trumbull, Conn.

[73] Assignee: International Research and Development Corp., Mattawan, Mich.

[21] Appl. No.: 65,664

[22] Filed: May 21, 1993

Related U.S. Application Data

[63] Continuation-in-part of Ser. No. 887,324, May 22, 1992, abandoned.

[51] Int. Cl.$^6$ .................................. A61K 7/42; A61K 7/44
[52] U.S. Cl. .................................. 424/59; 424/60; 424/65; 424/DIG. 5
[58] Field of Search .................................. 424/65, DIG. 5, 424/59, 60

[56] References Cited

U.S. PATENT DOCUMENTS

| | | | |
|---|---|---|---|
| 4,322,400 | 3/1982 | Yuhas | 424/59 |
| 4,650,670 | 3/1987 | Callingham et al. | 424/65 |
| 4,673,571 | 6/1987 | Mahieu et al. | 424/65 |
| 4,764,365 | 8/1988 | Boothe et al. | 424/65 |
| 4,985,547 | 1/1991 | Yano et al. | 514/846 |
| 5,025,004 | 6/1991 | Wu et al. | 424/60 |
| 5,039,516 | 8/1991 | Goodman et al. | 424/59 |

*Primary Examiner*—C. Warren Ivy
*Assistant Examiner*—Raymond Covington
*Attorney, Agent, or Firm*—The Firm of Gordon W. Hueschen

[57] ABSTRACT

A topical antiperspirant composition or preparation consisting essentially of an effective antiperspirant amount of a non-toxic water-insoluble occlusive film-forming polymer, and a method of reducing perspiration by applying such a composition to the skin of a subject in the area in which it is desired to reduce perspiration, is disclosed. A preferred polymer is an alkyl olefinic acid amide/olefinic acid or ester copolymer, e.g., octylacryl amide or propenamide/acrylates copolymer, alone or in combination with a PVP-linear alpha-olefin copolymer, especially a PVP/Eicosene copolymer or other water-repellant polymer. Normally-employed mineral salts, such as aluminum and zirconium chlorohydrate, may be included in the composition but, since not essential, may be employed in reduced amounts, if present. The composition may take various usual forms, such as solutions, suspensions, or other liquid forms, dab-ons, roll-ons, or stick forms, according to the convention of the art, with stick forms being preferred from the standpoint of extended and improved effectiveness. Evaporation of non-toxic solvent, in which the polymer may be dissolved or dispersed, leaves a cosmetically-acceptable and usually clear transparent antiperspirant film which is effective for its intended purpose.

43 Claims, No Drawings

TOPICAL ANTIPERSPIRANT COMPOSITION CONSISTING ESSENTIALLY OF NON-TOXIC WATER-INSOLUBLE OCCLUSIVE FILM-FORMING ANTIPERSPIRANT POLYMER

The present application is a continuation-in-part of my prior-filed U.S. application Ser. No. 07/887,324, filed May 22, 1992, now abandoned.

FIELD OF THE INVENTION

Topical antiperspirant compositions, in the present case containing no or a reduced quantity of a metal salt such as aluminum or zirconium chlorohydrate, but which essentially rely upon a non-toxic occlusive water-insoluble film-forming polymer for their primary antiperspirant activity and utility.

BACKGROUND OF THE INVENTION AND PRIOR ART

Antiperspirants are socially and cosmetically desirable products. Aluminum and zirconium chlorohydrates are Category I antiperspirant actives and products containing the same can be legally designated "antiperspirants". Other metal salts have been found to be effective, but have not found their way to the marketplace for many valid reasons. Anticholinergics, including scopolamine derivatives, are the most effective antiperspirants known. However, because of their poor skin-penetration properties, they require injections for effectiveness. Antiadrenergics have also been investigated, but have only developed academic interest. Aldehydes such as formaldehyde can suppress sweating, but their sensitization potential has eliminated commercialization. Metabolic inhibitors such as ouabain have been studied academically. Accordingly, at present, there is no really viable substitute for aluminum and zirconium chlorohydrates.

Antiperspirant compositions by definition must reduce or eliminate perspiration, at least in a designated area to which they are topically applied and, due to constant elevation of antiperspirant aims and objectives, are constantly increasing in their effectiveness, which by some standards must reduce perspiration by at least 20% in 50% of the population, although in many cases the attainment of such high percentage is not and may never be possible. Although numerous compositions have been proposed as antiperspirants, few of them have been successfully marketed because of their failure to provide effective antiperspirant relief or due to the production of irritation or other undesirable side effect and, after all these years, the most effective and successful antiperspirant compositions are still those comprising large proportions and amounts of aluminum or zirconium chlorohydrate or like mineral salts which retard the perspiration phenomenon, despite their frequently irritating nature and their undesirability from the standpoint of inherent toxicity.

Studies have been conducted and published concerning the anhydrosis effected by the application of various types of adhesive tape and tape-secured sheets of plastic to the skin and, although these investigations confirmed an anhydrosis effect, side-effects of an allergic nature as well as a mechanical nature and ensuing traumatic effects were also found to result. Moreover, in certain studies conducted on grants from the Army, the anhydrosis did not completely disappear and normal perspiration recover for a period of weeks after such application of the tape or plastic sheet for a period of only six (6) days. These studies, which seem mainly to have been directed at a determination of side effects of the procedure, did not in any event provide any effective measure or product for use as a topical antiperspirant, or apparently suggest any such preparation to those skilled in the art, over the period of approximately twenty-five years since appearance of the publications reporting the same. Specific identification of such known studies is as follows:

The first publication is entitled "Adhesive Tape Anhydrosis", by Gordon and Maibach, appearing in Arch. Derm. 100, 429–431 (October 1969), the study being supported by U.S. Army Research and Development Command, the earlier second reference being by Orentreich, Berger, and Auerbach, appearing in Arch. Derm. 94, 709–711 (December 1966), this publication being entitled "Anhydrotic Effects of Adhesive Tapes and Occlusive Film", and a third publication entitled "The Use of Partial Sweat Duct Occlusion in the Elucidation of Sweat Duct Function in Health and Disease", by Johnson and Shuster, J. Soc. Cosmet. Chem. 24, 15–29 (1973), which studied the effect of pressure due to occlusive tape on the sweat rate and the type of reabsorption involved, whether water or electrolyte. Nothing disclosed in those publications or suggested thereby comprises any part of the present invention, and reference is made thereto merely for purposes of completing the record. The innumerable publications and patents, which have appeared in the antiperspirant field since that date, attest to the fact that these publications did not change the direction of research in the field.

A search conducted in the antiperspirant classes, namely Class 424, Subclasses 65–68, 46, 47, Dig. 5 and IPC Class A61K7/32, turned up thirty (30) U.S. patents issued between 1978 and 1991, some of which included a polymer in the composition thereof, but only one of which consisted essentially of the polymer or relied upon the polymer to produce a desired antiperspirant effect. These developments employed the polymer merely as a means for adhering and/or maintaining the other chemical antiperspirant elements of the composition in contact with the skin of the human subject to which it was applied and in which an antiperspirant effect was desired to be attained, or relied upon an absorption phenomenon. Of all the patents turned up in the search, only U.S. Pat. Nos. 4,690,817, 4,743,440, 4,743,441, and 4,963,591 appeared to have any relevance to the present invention whatever.

The U.S. Pat. No. 4,690,817 patent related to the employment of polyvinyl alcohol polymers having pendant cationic quaternary nitrogen-containing groups to produce a film-forming moisture barrier for use in hair and skin conditioning compositions, which films were alleged to act as adhesives for the other composition components and as a partially impenetrable barrier to prevent loss of moisture by evaporation and to retain moisture through the formation of hydrates and no suggestion was made that such polymer or polymeric film would or could be useful as an antiperspirant per se.

The U.S. Pat. No. 4,743,440 patent related to antiperspirant products containing a moisture-absorbent non-film forming polymer instead of or in addition to the usual metal salt. The product was applied to the skin in a finely-divided powder form to give a dry, non-sticky deposit for absorbing skin moisture such as perspiration, the polymer being capable of absorbing an amount of moisture at least equal to its own weight after depositing the product onto the skin. The requisite characteristics of the polymer were that it be a non-film-forming polymer, and the composition comprised a non-aqueous liquid phase and a solid phase, as well as a propellant to produce an aerosol spray and a carrier other than a propellant for the organic polymer involved, the polymer involved in that case being a chemically-modified cellulose in particulate form, although polysaccharides, polypeptides, and vinylcarboxy polymers and copolymers were also mentioned as utilizable and numerous water-soluble and water-insoluble polymers were mentioned in Columns 3 and 4 of that patent as being suitable. Nothing is said in that patent concerning the occlusiveness of any polymer involved as having anything to do with its effectiveness as an antiperspirant, unless occlusiveness is equated with moisture absorbency, which it clearly is not in the present case.

U.S. Pat. No. 4,963,591 related to cellulosic polymer-solvent systems capable of dispersing a thin substantive film on the skin for cosmetic purposes and required the employment of a water-insoluble cellulosic ether for use in all kinds of lotions and creams designed for topical application, including deodorant and antiperspirant products, and alleged that the compositions of that invention could be applied to the skin wherever conditioning or treatment is desired by smoothing it over the skin, but made no claim whatever for the use of such films per se as an antiperspirant although it disclosed the employment of such polymers in sun screen-insect repellents and in solution in an aliphatic alcohol such as ethanol, propanol, or isopropanol along with other materials of an emollient nature and ordinarily employed in cosmetic preparations.

U.S. Pat. No. 4,743,441 disclosed the employment of a film-forming cosmetic composition as a facial pack, nail enamel, eyeliner, or the like comprising a copolymer of vinyl alcohol and alkyl vinyl ether, but made no claim to employment of such a composition per se or otherwise for antiperspirant purposes.

Additionally, U.S. Pat. No. 4,322,400, Yuhas; U.S. Pat. No. 4,985,547, Yano et al.; U.S. Pat. No. 5,025,004, Wu et al.; U.S. Pat. No. 5,039,516, Goodman et al.; U.S. Pat. No. 4,650,670, Callingham et al.; U.S. Pat. No. 4,673,571, Mahieu et al.; and U.S. Pat. No. 4,764,365, Boothe et al., have been called to my attention, but a study of the disclosures of these patents shows that they make no disclosure or suggestion of any topical antiperspirant composition consisting essentially of an effective amount of a non-toxic water-insoluble occlusive film-forming antiperspirant polymer in a topically-acceptable non-toxic medium, which is the subject matter of the present invention.

These prior-art teachings accordingly fall far short of the disclosure or suggestion of any concept of significance according to the present invention.

It is apparent that improved topical antiperspirant compositions have been the object of research over an extensive period, that the research has been mainly directed toward improved formulations of antiperspirant chemicals, that after all the years of research in this field mineral salts such as aluminum and zirconium chlorohydrates are still fundamentally relied upon for producing the desired antiperspirant effect of an antiperspirant composition or formulation in which they are present, and that efforts to eliminate the same from, or reduce the amount of the same in, the usual antiperspirant formulations have met with little if any success. Much less has any antiperspirant composition or formulation appeared on the scene which relied essentially upon the antiperspirant effect of a topically-applied non-toxic water-insoluble occlusive film-forming polymer, which is the essence of the present invention. It is also apparent that efforts to eliminate the undesirable mineral salts or reduce the quantity thereof necessary to produce a desired antiperspirant effect, or provide a viable alternative thereto, have been unsuccessful, and the present invention accordingly fulfills a long-felt need and shortcoming of the art, especially since the combined antiperspirant and deodorant market is now estimated at approximately 1.4 billion dollars per year.

OBJECTS OF THE INVENTION

It is an object of the present invention to provide new and useful topical antiperspirant compositions which are not dependent for their antiperspirant effectiveness upon the presence of a mineral salt such as aluminum or zirconium chlorohydrate, and a method of topically diminishing perspiration by the employment of such an improved and novel antiperspirant composition to the skin of a subject in the area in which diminished perspiration is desired to be effected. Another object of the invention is to provide an improved topical antiperspirant composition consisting essentially of a non-toxic water-insoluble occlusive film-forming antiperspirant polymer and a method of topically diminishing perspiration by the application of a topical film of such polymer to the skin of the subject by the application of such a composition or formulation thereto. Still another object of the invention is to provide such a topical antiperspirant composition consisting essentially of the non-toxic water-insoluble occlusive film-forming antiperspirant polymer and a method of topically diminishing perspiration by the employment thereof, as just stated, wherein the composition optionally but preferably and advantageously also contains a water-proofing agent or water-repellant polymer, especially of the type disclosed hereinafter. A further object of the invention is the provision of such a composition and method wherein diminished or reduced amounts of the usual mineral salts may be employed due to the essential presence of an effective antiperspirant amount of a water-insoluble occlusive film-forming amount of a non-toxic polymer to produce an effective topical occlusive antiperspirant film thereof on the skin of the subject. Additional objects of the invention will become apparent hereinafter and still others will be obvious to one skilled in the art as the description proceeds.

SUMMARY OF THE INVENTION

The invention comprises a non-metallic salt antiperspirant based upon a film-forming water-insoluble occlusive cosmetically-acceptable and non-toxic skin-safe antiperspirant polymer composition. Such polymers or combinations thereof can be from any class of chemical compounds which produce low-porosity skin-adhering non-irritant water-insoluble occlusive films which reduce under-arm perspiration. A wide variety of vinyl or acrylic copolymers have suitable properties, which polymers, combinations, and compositions can be tailored to demand once the disclosure of this invention becomes known. In addition to the film-formers, the novel compositions can include anti-microbial agents to increase deodorant activity, fragrances to enhance deodorancy, and various cosmetic ingredients to perform as part of the vehicle to provide various physical forms of antiperspirants with cosmetic acceptability. Such compositions optionally but advantageously also include the presence of a waterproofing or water-repellant polymer, as previously disclosed and as will be further disclosed in more detail hereinafter. Such forms include sprays, dab-o-matics, roll-ons, and sticks, produced generally in a manner well-known in the art, for example, as evidenced by the aforementioned U.S. patents. For increased antiperspirant activity and duration, combinations of polymer and reduced levels of metallic salts, e.g., aluminum or zirconium salts, e.g. the chlorohydrates, can be formulated. According to the invention, the selected polymer is usually at least partially dissolved or suspended in a non-toxic solvent and applied in solution or suspension form, even when in the form of a solid stick, to the area in which perspiration is desired to be prevented or diminished and, regardless of the exact form in which applied, the solvent allowed to evaporate, thereby producing the occlusive antiperspirant film upon the skin surface.

The invention, then, inter alia, comprises the following, alone or in combination:

A topical antiperspirant composition consisting essentially of an effective amount of a non-toxic water-insoluble occlusive film-forming antiperspirant polymer in a topically-acceptable non-toxic medium; such a composition wherein the polymer is in solution or dispersion in said medium; such a composition wherein the medium is a non-toxic topically-acceptable medium which acts as solvent for the polymer and which evaporates after application to leave a film of the polymer; such a composition wherein the polymer is dissolved or dispersed in a non-toxic topically-acceptable alcohol or ketone; such a composition wherein the medium is selected from a lower-aliphatic alcohol and a lower-aliphatic ketone; such a composition wherein the medium is selected from the group consisting of ethyl alcohol, isopropyl alcohol, n-propanol, n-butanol, sec. butanol, isobutanol, and acetone; such a composition wherein the composition includes a topically-acceptable carrier, diluent, or excipient; such a composition wherein the composition comprises a vinyl or acrylic copolymer and is in liquid, roll-on, stick form, or dab-on form; such a composition wherein the polymer comprises an alkyl olefinic acid amide/olefinic acid or ester copolymer alone or in combination with a water-repellant polymer; such a composition wherein the polymer comprises an octylacrylamide or propenamide/acrylates copolymer alone or in combination with a water-repellant polymer; such a composition wherein the polymer comprises an alkyl olefinic acid amide/olefinic acid or ester copolymer alone or with a PVP/linear alpha-olefin copolymer; such a composition wherein the polymer comprises an octylacrylamide or propenamide/acrylates copolymer alone or with a PVP/linear alpha-olefin copolymer; such a composition wherein the polymer comprises an octylacrylamides/acrylates copolymer alone or in combination with a PVP/linear alpha-olefin copolymer; such a composition wherein the polymer comprises between about 5% and about 40% by weight; such a composition wherein the polymer comprises between about 5% and about 40% by weight, bodying agent between about 5% and about 35% by weight, emollient-plasticizer-cosolvent between about 5% and about 25% by weight, and solvent for the polymer between about 30% and about 80% by weight; such a composition wherein the polymer comprises an alkyl olefinic acid amide/olefinic acid or ester copolymer alone or with a PVP/linear alpha-olefin copolymer; such a composition wherein the polymer comprises an octylacrylamide or propenamide/acrylates copolymer alone or with a PVP/linear alpha-olefin copolymer; such a composition wherein the polymer comprises an octylacrylamides/acrylates copolymer alone or in combination with a PVP/Eicosene copolymer; such a composition wherein the polymer comprises a vinyl acetate/butyl maleate/isobornyl acrylates copolymer alone or in combination with a waterproofing agent; such a composition wherein the polymer comprises a vinyl acetate/butyl maleate/isobornyl acrylates copolymer alone or in combination with a PVP/linear alpha-olefin copolymer, and finally such a composition wherein the polymer comprises a vinyl acetate/butyl maleate/isobornyl acrylates copolymer alone or in combination with a PVP/Eicosene copolymer.

Moreover, a method of topically reducing perspiration in a subject consisting essentially of the step of topically applying to the skin of the subject in the area in which it is desired to reduce perspiration a topical antiperspirant composition consisting essentially of an effective amount of a non-toxic water-insoluble occlusive film-forming antiperspirant polymer in a topically-acceptable non-toxic medium; such a method wherein the composition applied to the skin of the subject comprises the polymer plus a non-toxic topically-acceptable medium which acts as solvent for the polymer and wherein after application the solvent is evaporated to leave a film of the polymer; such a method wherein the polymer is in solution or dispersion in said medium; such a method wherein the medium is a non-toxic topically-acceptable medium which acts as solvent for the polymer and which evaporates after application to leave a film of the polymer; such a method wherein the polymer is dissolved or dispersed in a non-toxic topically-acceptable alcohol or ketone; such a method wherein the medium is selected from a lower-aliphatic alcohol and a lower-aliphatic ketone; such a method wherein the medium is selected from the group consisting of ethyl alcohol, isopropyl alcohol, n-propanol, n-butanol, sec. butanol, isobutanol, and acetone; such a method wherein the composition includes a topically-acceptable carrier, diluent, or excipient; such a method wherein the composition comprises a vinyl or acrylic copolymer and is in liquid, roll-on, stick form, or dab-on form; such a method wherein the polymer comprises an alkyl olefinic acid amide/olefinic acid or ester copolymer alone or in combination with a water-repellant polymer; such a method wherein the polymer comprises an octylacrylamide or propenamide/acrylates copolymer alone or in combination with a water-repellant polymer; such a method wherein the polymer comprises an alkyl olefinic acid amide/olefinic acid or ester copolymer alone or with a PVP/linear alpha-olefin copolymer; such a method wherein the polymer comprises an octylacrylamide or propenamide/acrylates copolymer alone or with a PVP/linear alpha-olefin copolymer; such a method wherein the polymer comprises an octylacrylamides/acrylates copolymer alone or in combination with a PVP/linear alpha-olefin copolymer; such a method wherein the polymer comprises between about 5% and about 40% by weight; such a method wherein the polymer comprises between about 5% and about 40% by weight, bodying agent between about 5% and about 35% by weight, emollient-plasticizer-cosolvent between about 5% and about 25% by weight, and solvent for the polymer between about 30% and about 80% by weight; such a method wherein the polymer comprises an alkyl olefinic acid amide/olefinic acid or ester copolymer alone or with a PVP/linear alpha-olefin copolymer; such a method wherein the polymer comprises an octylacrylamide or propenamide/acrylates copolymer alone or with a PVP/linear alpha-olefin copolymer; such a method wherein the polymer comprises an octylacrylamides/acrylates copolymer alone or in combination with a PVP/Eicosene copolymer; such a method wherein the polymer comprises a vinyl acetate/butyl maleate/isobornyl acrylates copolymer alone or in combination with a waterproofing agent; such a method wherein the polymer comprises a vinyl acetate/butyl maleate/isobornyl acrylates copolymer alone or in combination with a PVP/linear alpha-olefin copolymer, and finally such a method wherein the polymer comprises a vinyl acetate/butyl maleate/isobornyl acrylates copolymer alone or in combination with a PVP/Eicosene copolymer.

GENERAL DESCRIPTION OF THE INVENTION

For purposes of the present invention, the polymer must be a film-forming, water-insoluble, and occlusive polymer, the term "occlusive" having the meaning set forth in Webster's 3rd New International Dictionary, G and C Merriam Company, Publishers, Springfield, Mass. (1963) at page 1560, where the term "occlusive" means "serving to occlude" and the term "occlusion" means a shutting off or obstruction of something, in this case perspiration, whether by shutting off the ducts or the glands, this being immaterial from the standpoint of the present invention, as long as the perspiration is shut off, and presumably surface perspiration is shut off from its source comprising the glands and the ducts. This is not to be confused with an absorption phenomenon, whereby the polymer merely absorbs the moisture created by the perspiration, as should immediately be apparent to one skilled in the art.

A topical antiperspirant composition or preparation consisting essentially of an effective antiperspirant amount of a non-toxic water-insoluble occlusive film-forming antiperspirant polymer, and a method of reducing perspiration by applying such a composition to the skin of a subject in the area in which it is desired to reduce perspiration, such as the armpits, is disclosed. A waterproofing agent or water-repellant polymer, such as the Ganex polymers disclosed hereinafter, is optionally but preferably and advantageously included in the compositions employed according to the present invention. Normally-employed mineral salts, such as aluminum and zirconium chlorohydrate, may be included in the composition but, since not essential, may be employed in reduced amounts, if present. The composition may take various usual forms, such as solutions, suspensions, or other liquid forms, dab-ons, roll-ons, or stick forms, according to the convention of the art, with stick forms being preferred from the standpoint of extended and improved effectiveness. Evaporation of non-toxic solvent, in which the polymer may be dissolved or dispersed, and which is in any case ordinarily present in the composition, even when in stick form, leaves a cosmetically-acceptable and usually clear transparent antiperspirant film which is effective for its intended purpose. When an antiperspirant polymer employed is relatively incompatible in the vehicle or composition form employed, due to fragility or the like, the antiperspirant polymer may be encapsulated in another polymer, as by coacervation or other conventional technique, so that the active antiperspirant polymer may be released from its encapsulated form upon contact when applied under pressure.

DETAILED DESCRIPTION OF THE INVENTION

The following Examples are given to illustrate the compositions or formulations and the method of the present invention, but are not to be construed as limiting.

Various formulas have been developed, each exhibiting a significant reduction in perspiration due to the occlusive film produced on the under-arms (i.e., armpits) of the subjects involved in the testing procedure, which among other things has involved a hot room or modified sauna test study, to evaluate the prototypes and improved modifications thereof, with improvements in providing a less tacky film and a more flexible film being among the objectives of the formulation variations. Reductions in under-arm perspiration have ranged from the approximately 12% reduction in perspiration employing liquid formula FT-5-015, through the 17% reduction in perspiration from the occlusive film produced on the under-arms with the employment of dab-on formula FT-4-001, up through the advanced stick formula FT-8-014B, which produced more than a 34% reduction in perspiration. Maximum perspiration reduction was greater than 50%, as will be seen from the following.

EXAMPLE 1

Dab-on Antiperspirant Formula—FT-4-001

Preparation Procedure:
1. Place the alcohol in a pre-weighed beaker containing a stir bar.
2. Start stirring.
3. Add Versatyl-42 slowly so that no accumulation of polymer occurs on the surface.
4. After all of the Versatyl-42 has been added, continue stirring until the polymer has dissolved.
5. Add the remaining ingredients and stir until the solution is clear.
6. Check for alcohol loss and then dispense.

| CTFA Name | % By Weight |
| --- | --- |
| OctylAcrylamide/Acrylates Copolymer | 10 |
| Triclosan | 0.1 |
| Fragrance #31278 | 0.5 |
| Isopropyl Alcohol, 99% | 89.4 |
| | 100.0 |

EXAMPLE 2

Roll-On Antiperspirant—Formula FT-5-015

Preparation Procedure:
Follow the procedure used for FT-4-001. (See Example 1.)

| CTFA Name | % By Weight |
| --- | --- |
| OctylAcrylamide/Acrylates Copolymer | 15 |
| PPG-10 Methyl Glucose Ether | 5 |
| Triclosan | 0.25 |
| Fragrance #31278 | 0.5 |
| S.D. Alcohol Formula #40 | 79.25 |
| | 100.00 |

EXAMPLE 3

Stick Form Antiperspirant—FT-8-014B (aka FT-8-020) (also FT-8-035)

Preparation Procedure:
1. Place the SDA-40 in a pre-weighed beaker containing a stir bar.
2. Start stirring.
3. Add Versatyl-42 slowly so that no accumulation of polymer occurs on the surface.
4. After all of the Versatyl-42 has been added, continue stirring until the polymer has dissolved.
5. Add Steareth-2, PVP/Eicosene Copolymer, Stearyl Alcohol, and Cetyl Acetate/Acetylated Lanolin Alcohol.
6. Heat solution to 75° C.
7. Once all waxes have melted, remove from heat and begin stirring.
8. Cool to 55° C. while stirring.
9. Add Triclosan and Fragrance and continue stirring until solution is clear.
10. Form into desired shape in suitable mold according to conventional procedure.

| CTFA Name | % By Weight |
| --- | --- |
| FT-8-020 | |
| Octylacrylamide/Acrylates Copolymer | 10 |
| Steareth-2 | 6 |
| PVP/Eicosene Copolymer (waterproofer) | 13 |
| Stearyl Alcohol | 20 |
| Cetyl Acetate/Acetylated Lanolin Alcohol | 10.7 |
| Triclosan | 0.2 |
| Fragrance #31278 | 0.5 |
| S.D. Alcohol Formula #40 | 39.6 |
| | 100.0 |
| FT-8-035 | |
| Octylacrylamide/Acrylates Copolymer | 7.5 |
| Steareth-2 | 8.5 |
| PVP/Eicosene Copolymer (waterproofer) | 13 |
| Stearyl Alcohol | 20 |
| Cetyl Acetate/Acetylated Lanolin Alcohol | 10.7 |
| Triclosan | 0.2 |
| Fragrance #31278 | 0.5 |
| S.D. Alcohol Formula #40 | 39.6 |
| | 100.0 |

The ingredients of the foregoing Example 3 were stable and perfectly soluble in the alcohol employed when hot and, when cooled, solidified rapidly into a stick which was topically-acceptable and entirely satisfactory from the standpoint of application to the armpit. In place of the S.D. Alcohol Formula #40, ordinary ethyl alcohol, denatured ethyl alcohol, isopropyl alcohol, acetone, or other nontoxic solvent, such as n-butanol, sec. butanol, isobutanol, or n-propanol, may be employed, in which the selected polymer can be dissolved or dispersed and, if desired, in which the optional aluminum or zirconium chlorohydrate or other salt may be conveniently dissolved.

EXAMPLE 4

| FT-8-039 - Stick Formula | % By Weight |
| --- | --- |
| Tradename | |
| Ethyl Alcohol, 95% v/v | 39.5 |
| PVP/Eicosene copolymer (waterproofer) | 13.0 |
| Stearyl Alcohol | 11.0 |
| Cetyl Acetate/Acetylated Lanolin Alcohol | 10.7 |
| Sodium Stearate | 9.0 |
| Steareth-2 | 8.5 |
| Octylacrylamide/Acrylates copolymer | 7.5 |
| Fragrance | 0.5 |
| Triclosan | 0.3 |
| | 100.0 |

EXAMPLE 5

Additional Preparations

The following prototype formulations have been evaluated in hot room studies and exhibited less than 20% sweat reduction:

| | % By Weight |
| --- | --- |
| FT-4-027 | |
| Ethyl Alcohol (special denatured Formula #40) | 88.58 |
| Carboset 525™ (Acrylic Copolymer) | 5.0 |
| Versatyl 42 (Octylacrylamide/Acrylates Copolymer) | 5.0 |
| Triethanolamine | 0.72 |
| Fragrance | 0.5 |
| Irgasan DP-300 (Triclosan) | 0.2 |
| | 100.0 |
| FT-4-068 | |
| Ethyl Alcohol, 95% v/v | 89.3 |
| Carboset 525™ | 7.25 |
| Versatyl 42 | 2.5 |
| Fragrance | 0.5 |
| Irgasan DP-300 | 0.2 |
| | 100.0 |
| FT-5-049 | |
| Ethyl Alcohol, 95%v/v | 79.3 |
| Luviflex VBM - 35™ (PVP/Acrylates Copolymer) | 20.0 |
| Fragrance | 0.5 |
| Irgasan DP-300 | 0.2 |
| | 100.0 |

EXAMPLE 6

Still Additional Preparations

The following prototype formulations are also effective in sweat reduction:

| FT-5-047D | % By Weight |
|---|---|
| Ethyl Alcohol, 95% v/v | 52.0 |
| Stearyl Alcohol | 20.0 |
| Dermacryl 79™ (Acrylates/t-Octylpropenamide Copolymer) | 15.0 |
| Ganex V-220™ (PVP/Eicosene Copolymer) | 13.0 |
| | 100.0 |

| FT-5-047E | |
|---|---|
| Ethyl Alcohol, 95% v/v | 47.0 |
| Luviflex VBM-35™ | 20.0 |
| Stearyl Alcohol | 20.0 |
| Ganex V-220 (water-repellant polymer) | 13.0 |
| | 100.0 |

EXAMPLE 7

Other Additional Preparations

The following prototype formulations have also been prepared and are effective in sweat reduction:

| FT-4-013 | % By Weight |
|---|---|
| Ethyl Alcohol, 95% v/v | 74.3 |
| Stepanhold Extra™ (PVP/Ethyl Methacrylate/Methacrylic Acid Terpolymer) | 25.0 |
| Fragrance | 0.5 |
| Irgasan DP-300 | 0.2 |
| | 100.0 |

| FT-4-015 | |
|---|---|
| Ethyl Alcohol, 95% v/v | 79.3 |
| Gantrez SP-215™ (Ethyl Ester of PVM/MA Copolymer) | 20.0 |
| Fragrance | 0.5 |
| Irgasan DP-300 | 0.2 |
| | 100.0 |

| FT-4-017 | |
|---|---|
| Ethyl Alcohol, 95% v/v | 79.3 |
| Ucarset LP-250 (Ethyl Ester of PVM/MA Copolymer) | 20.0 |
| Fragrance | 0.5 |
| Irgasan DP-300 | 0.2 |
| | 100.0 |

EXAMPLE 8

Prototype Examples With Ranges

| CTFA Name | % By Weight Range |
|---|---|
| A. Prototype Dab-on or Spray Antiperspirant Formula | |
| Antiperspirant Polymer, e.g., Alkyl Olefinic acid amide/olefinic acid or ester copolymer such as Octylacryl amide or propenamide/acrylates Copolymer (or other perspiration-reducing polymer) | 2.5–25 preferably 5–20 |
| Triclosan (antimicrobial) | 0.00–1 |
| Fragrance | 0.00–1 |
| Isopropyl Alcohol (95–99%) or specially denatured ethyl alcohol #40 (95%) (polymer solvent) | 97.45–78 |
| B. Prototype Roll-on Antiperspirant Formula | |
| Antiperspirant Polymer, e.g., Alkyl Olefinic acid amide/olefinic acid or ester copolymer such as Octylacryl amide or propenamide/acrylates Copolymer (or other perspiration-reducing polymer) | 2.0–25 preferably 5–20 |
| PPG-10 Methyl Glucose Ether (moisturizer-emollient) | 1–10 |
| Triclosan (antimicrobial) | 0.00–1 |
| Fragrance | 0.00–1 |
| Isopropyl Alcohol (95–99%) or specially denatured ethyl alcohol #40 (95%) (polymer solvent) | 97–68 |
| C. Prototype Stick Antiperspirant | |
| Antiperspirant Polymer, e.g., Alkyl Olefinic acid amide/olefinic acid or ester copolymer such as Octylacryl amide or propenamide/acrylates Copolymer (or other perspiration-reducing polymer) | 2–25 preferably 5–20 |
| Steareth-2 (solubilizer) | 2.0–10.0 |
| PVP/Linear Alpha-Olefin Copolymer, e.g., PVP/Eicosene Copolymer (or other water-repellent polymer) | 5.0–20.0 |
| Stearyl Alcohol (bodying agent) | 5.0–20.0 |
| Sodium Stearate (bodying agent) | 0.0–15.0 |
| Cetyl Acetate/Acetylated Lanolin Alcohol or Tricontanyl PVP (emollient-plasticizer-cosolvent) | 5.0–20.0 |
| Triclosan (antimicrobial) | 0.00–1.0 |
| Fragrance | 0.00–1.0 |
| Isopropyl Alcohol (95–99%) or specially denatured ethyl alcohol #40 (95%) (polymer solvent) | 80.0–30.0 |

| Composition: | |
|---|---|
| Stearyl alcohol | High melting bodying agent |
| Ethyl alcohol | Polymer solvent |
| Acetylated lanolin alcohol | Emollient-plasticizer and cosolvent |
| PVP/linear Alpha-olefin copolymer, e.g., PVP/Eicosene copolymer | Water-repellent polymer |
| Steareth-2 | Solubilizer |
| Alkyl olefinic acid amide/ olefinic acid or ester copolymer, e.g., Octyl-acrylamide/acrylates copolymer | Perspiration-reducing polymer |
| Fragrance | Characteristic fragrance |
| Triclosan | Antibacterial agent |

For best results, the antiperspirant polymer should be occlusive, be water-insoluble and have low water permeability, a high degree of adhesion, be non-toxic, and to at least a limited extent flexible, at least in monomolecular films or films approaching the same and, in the stick form of antiperspirant, the conventional additional materials are usually of a waxy nature and add plasticity and bulk to the stick form of the antiperspirant product, as is well known in the art.

The octylacrylamide/acrylates copolymer advantageously provides the perspiration-reducing polymer of the invention. The PVP/Eicosene water-repellant copolymer improves the effectiveness of the octylacrylamide/acrylates copolymer. Other water-repellant polymers, and especially PVP/linear alpha-olefin copolymers, may be used instead of the PVP/Eicosene copolymer, e.g., PVP/hexadecene copolymer, with equivalent results.

Specific Characteristics a. Applies easily with good rub-off.
b. Effectively reduces perspiration.
c. Helps prevent bacterial decomposition of perspiration.
d. Imparts characteristic fragrance to underarms.
e. Non-irritating to normal skin.

Superiorities a. Non-aluminum/zirconium chlorohydrate antiperspirant.
b. Effective antiperspirant and deodorant.
c. Non-irritating to normal skin.
d. Applies easily.

Suggested Directions for Use

Use daily after bathing.
Remove cap and surface seal and propel stick above lip of container. Apply to entire underarm. Lower stick, replace surface seal, and recap tightly after use to prevent dryout. If stick surface becomes very dry, scrape off a thin layer before applying.
Warning: Do not apply to broken, irritated, or sensitive skin. If rash or irritation develops, discontinue use. Keep out of reach of children.

Limitations a. Product is tacky until film dries. Talc can be applied to underarms to expedite drying.
b. Product contains alcohol which can cause stinging on freshly-shaved skin.
c. Product has a relatively low melting point so should not be exposed to high temperatures.
d. Product contains alcohol (solvent) which requires tight packaging to prevent excess weight loss and product dryout.

Pharmacological/Clinical Evaluation (Hot room or modified sauna procedure)

The hotroom or sauna testing procedure was as follows:

Sauna or Hotroom Evaluation

According to the present invention, once a polymer had been established as being non-toxic, skin-safe, to exhibit good adhesion, flexibility, and occlusivity upon preliminary screening, formulations were prepared for preliminary stability and effectiveness testing and were then evaluated according to panelists in a modified sauna evaluation, the sauna being maintained at 100° F. and a 35% relative humidity in accord with procedures submitted to the FDA by the OTC review panel for the evaluation of OTC antiperspirant drug products in August of 1982.

The results of the modified sauna evaluations are reported herein where available.

A. FT-8-020 with 10% Versatyl-42 in a stick base was evaluated in the modified sauna evaluation phase and found to exhibit 30–37% sweat reduction at a 95% confidence level.

FT-8-020 questionnaire results were as follows:

| Deodorant protection: | Yes - 21  No - 7 |
|---|---|
| Deodorant protection vs. their own: | Better - 6 |
| | Same - 13 |
| | Worse - 9 |
| Antiperspirant protection: | Yes - 22  No - 6 |
| Antiperspirant protection vs. their own: | Better - 5 |
| | Same - 14 |
| | Worse - 9 |

B. In view of the favorable results with the foregoing, preparation FT-8-035, a 7.5% Versatyl-42 polymer composition in a stick base (see Example 3), was formulated and tested satisfactorily by observation of the data and subjected to modified sauna testing.

FT-8-035, 7.5% polymer level, exhibited 31–41% sweat reduction at 95% confidence interval.

FT-8-035 Questionnaire results:

| Deodorant protection: | Yes - 25  No - 6 |
|---|---|
| Deodorant protection vs. their own: | Better - 6 |
| | Same - 16 |
| | Worse - 9 |
| Antiperspirant protection: | Yes - 26  No - 5 |
| Antiperspirant protection vs. their own: | Better - 6 |
| | Same - 15 |
| | Worse - 10 |

C. In a repeat of the Modified Sauna Evaluation for FT-8-035, 7.5% polymer, it exhibited 41–48% sweat reduction at 95% confidence interval.

FT-8-035 Questionnaire results:

| Deodorant protection: | Yes - 21  No - 8 |
|---|---|
| Deodorant protection vs. their own: | Better - 6 |
| | Same - 13 |
| | Worse - 13 |
| Antiperspirant protection: | Yes - 22  No - 7 |
| Antiperspirant protection vs. their own: | Better - 6 |
| | Same - 13 |
| | Worse - 10 |

D. A Modified Sauna Evaluation of stick formula FT-8-039 (see Example 4), a modification of FT-8-035 with improved stability, was undertaken and completed. Statistical results with a 95% confidence interval gave sweat reductions with a mean of 45.9, a low of 40.7 and a high of 50.7.

In a Modified Sauna Evaluation for FT-8-037, a currently marketed Stick Antiperspirant, the product exhibited only a 14.2% sweat reduction at a 95% confidence interval.

EXAMPLE 9

Additional Antiperspirant Formulas—FT-4-032, 4-091, 4-092, 4-093—with usual antiperspirant active

Preparation Procedure

1. Place the alcohol in a pre-weighed beaker containing a stir bar.

2. Start stirring.
3. Add Rehydrol II and stir until completely dissolved.
4. Add polymer slowly and continue stirring until the solution is clear.
5. Add the remaining materials and stir until the solution is clear.
6. Check for alcohol loss and then dispense.

| Trade Name | % By Weight |
|---|---|
| a. FT-4-032A | |
| Versatyl-42 | 5.00 |
| Rehydrol II or Al or Zr chlorohydrate | 5.00 |
| Irgasan DP-300 | 0.20 |
| #31278 Fragrance | 0.50 |
| S.D. Alcohol Formula #40 | 89.30 |
| | 100.00 |
| b. FT-4-091 | |
| Luviflex VBM-35 (50% polymer in EToH) | 10.00 |
| Rehydrol II | 10.00 |
| Irgasan DP-300 | 0.20 |
| #31278 Fragrance | 0.50 |
| S.D. Alcohol Formula #40 | 79.30 |
| | 100.00 |
| c. FT-4-092 | |
| Luviflex VBM-35 (50% polymer in EtoH) | 10.00 |
| Rehydrol II | 15.00 |
| S.D. Alcohol Formula #40 | 75.00 |
| | 100.00 |
| d. FT-4-093 | |
| Luviflex VBM-35 (50% polymer in EtoH) | 10.00 |
| Rehydrol II | 5.00 |
| Irgasan DP-300 | 0.20 |
| #31278 Fragrance | 0.50 |
| S.D. Alcohol Formula #40 | 84.30 |
| | 100.00 |

Since an evaluation of our prototype testing, conducted at a well-recognized testing facility, confirmed our findings of validity and reliability, we have continued to utilize our modified Sauna test procedure using approximately 12 panelists (⅓ the size of our earlier panels).

EXAMPLE 10

| Phase 16 Prototype FT-9-025 (stick form) | % By Weight |
|---|---|
| Ethyl Alcohol, 95% v/v | 39.5 |
| Dermacryl 79 (Acrylates//t-Octylpropenamide Copolymer) | 7.5 |
| Irgasan DP-300 | 0.3 |
| Fragrance | 0.5 |
| Steareth 2 | 8.5 |
| Cetyl Acetate/Acetylated Lanolin Alcohol | 10.7 |
| Stearyl Alcohol | 11.0 |
| Sodium Stearate | 9.0 |
| PUP/Eicosene Copolymer (water-repellant polymer) | 13.0 |
| | 100.00 |

Stick FT-9-025 Modified Sauna results were statistical reductions in perspiration of a low of 26.5% to a high of 39.1% with a mean of 33.1% and a median of 23.8% at a 95% confidence level.

EXAMPLE 11

Antiperspirant Study #999-064

| Phase 16A Prototype FT-9-026 (stick form) | By Weight |
|---|---|
| Ethyl Alcohol, 95% v/v | 39.5 |
| Amphomer LV-71 (Octylacrylamide/Acrylates/Butylaminoethyl Methacrylate Copolymer) | 7.5 |
| Irgasan DP-300 | 0.3 |
| Fragrance | 0.5 |
| Steareth 2 | 8.5 |
| Cetyl Acetate/Acetylated Lanolin Alcohol | 10.7 |
| Stearyl Alcohol | 11.0 |
| Sodium Stearate | 9.0 |
| PUP/Eicosene Copolymer (water-repellant polymer) | 13.0 |
| | 100.0 |

Stick FT-9-026 Modified Sauna results with 12 panelists gave reductions in perspiration between a low of 8.7% and a high of 29%, with a mean of 19.5% and a median of 15.4%. Questionnaires resulted in 11 qualifying test panelists indicating that the test product was an effective antiperspirant with 4 rating better, 6 same, and 2 worse than their own product.

EXAMPLE 12

Antiperspirant Study #999-064

| Phase 16B Prototype FT-9-027 (stick form) | By Weight |
|---|---|
| Ethyl Alcohol, 95% v/v | 39.5 |
| Amphomer (Octylacrylamide/Acrylates/Butylaminoethyl Methacrylate Copolymer) | 7.5 |
| Irgasan DP-300 | 0.3 |
| Fragrance | 0.5 |
| Steareth 2 | 8.5 |
| Cetyl Acetate/Acetylated Lanolin Alcohol | 10.7 |
| Stearyl Alcohol | 11.0 |
| Sodium Stearate | 9.0 |
| PUP/Eicosene Copolymer (water-repellantpolymer) | 13.0 |
| | 100.0 |

Stick FT-9-027 Modified Sauna results gave statistical reductions in perspiration between a low of 18.3% and a high of 32.7% with a mean of 25.8% and a median of 25.3% at a 95% confidence level.

EXAMPLE 13

Antiperspirant Study #999-064

| Phase 16C Prototype FT-9-029 (stick form) | By Weight |
|---|---|
| Ethyl Alcohol, 95% v/v | 32.0 |
| Advantage CP, 50% (Copolymer of vinyl acetate, butyl maleate and isobornyl acrylate) | 15.0 |
| Irgasan DP-300 | 0.3 |
| Fragrance | 0.45 |
| Steareth 2 | 8.5 |
| Cetyl Acetate/Acetylated Lanolin Alcohol | 10.7 |
| Stearyl Alcohol | 11.0 |
| Sodium Stearate | 7.0 |
| PUP/Eicosene (water-repellant polymer) | 10.0 |
| Carbomer 1342 (Acrylic Acid Copolymer) | 0.05 |
| Glyceryl hydroxystearate | 5.0 |
| | 100.0 |

The data was analyzed by Analysis of Covariance. The resulting confidence limits are:

95% confidence interval for treated rate/control rate

| Lower limit: | 17.2% |
|---|---|
| Mean: | 21.5% |
| Upper limit: | 25.6% |

Therefore, Median Sweat Reduction was 20.6%.

Carbomer 1342 or similar polymer may advantageously be employed as a stabilizer to minimize syneresis or bleeding of fluid from within a solid stick form of the antiperspirant composition as presented in this Example 13 or other stick formulations.

EXAMPLE 14

Antiperspirant Study #999-064

| Phase 16D Prototype FT-9-030 (stick form) | By Weight |
|---|---|
| Ethyl Alcohol, 95% v/v | 39.5 |
| Carboset 525 (Acrylic-acrylate copolymer) | 2.5 |
| Amphomer LV-71 (Octylacrylamide/Acrylates/Butylaminoethyl Methacrylate Copolymer) | 7.5 |
| Irgasan DP-300 | 0.3 |
| Fragrance | 0.5 |
| Steareth 2 | 8.5 |
| Cetyl Acetate/Acetylated Lanolin Alcohol | 10.7 |
| Stearyl Alcohol | 8.5 |
| Sodium Stearate | 9.0 |
| PUP/Eicosene Copolymer (water-repellant polymer) | 13.0 |
| | 100.0 |

The data was analyzed by Analysis of Covariance. The resulting confidence limits are:

95% confidence interval for treated rate/control rate

| Lower limit: | 29.9% |
|---|---|
| Mean: | 35.6% |
| Upper limit: | 40.9% |

Therefore, Median Sweat Reduction was 34.1%

Preferred Polymers and Polymers Evaluated:

| Trade Name | CTFA Designation |
|---|---|
| Versatyl 42 | Octylacrylamide/AcrylatesCopolymer |
| Amphomer | Octylacrylamide/Acrylates/Butyl-aminoethyl Methacrylate Copolymer |
| Luviflex VBM - 35 | PVP/Acrylates Copolymer |
| Amphomer LV-71 | Octylacrylamide/Acrylate Copolymer (CTFA name: Same as Amphomer) |
| Dermacryl-79 | Acrylates/t-Octylpropenamide Copolymer |
| Resyn 28-1310 | Vinyl Acetate/Crotonic Acid Copolymer |
| Resyn 28-2913 | Vinyl Acetate/Crotonic Acid/Vinyl Neodecanoate Copolymer |
| Resyn 28-2930 | Vinyl Acetate/Crotonic Acid/Vinyl Neodecanoate Copolymer |
| Versacryl-40 | Octylacrylamide/AcrylatesCopolymer |
| Ucarset LP-250 | Ethyl Ester of PVM/MA Copolymer |
| Ganex V-516 | PVP/Hexadecene Copolymer |
| Ganex V-216 | PVP/Hexadecene Copolymer (waterproofer) (Av. MW ca. 7,300) |
| Ganex V-220 | PVP/Eicosene Copolymer (waterproofer) (Av. MW ca. 8,600) |
| Gantrez ES-225 | Ethyl Ester of PVM/MA Copolymer |
| Gantrez ES-425 | Butyl Ester of PVM/MA Copolymer |
| Gantrez SP-215 | Monoethyl Ester of (Methyl Vinyl Ether/Maleic Acid) |
| Stepanhold Extra | PVP/Ethyl Methacrylate/Methacrylic Acid Terpolymer |
| Carboset 525 | Acrylic/Acrylate Copolymer |
| Luviflex VMB-35 | PVP/Acrylates Copolymer |
| Ganex P-904 | Butylated PVP |
| Ganex WP-660 | 2-Pyrrolidinone, 1-Ethenyl-Polymer with 1-Triacontene |
| Gantrez AD-119 | PVP/MA Copolymer |
| Gantez MS-955 | 2-Butenedioic Acid (2); Polymer with Methoxyethene Calcium, Sodium Salt |
| PVP/VA E-335 | PVP/VA Copolymer |
| PVP/VA E-635 | PVP/VA Copolymer |
| PVP/VA E-735 | PVP/VA Copolymer |
| ADVANTAGE CP | Vinyl acetate, butyl maleate, and isobornyl acrylate |
| Carbomer 1342 | Acrylic acid copolymer |

FURTHER IDENTIFICATION OF PRODUCTS PREVIOUSLY IDENTIFIED BY TRADE NAME OR CTFA DESIGNATION OR OTHERWISE, WHERE AVAILABLE

If carboxyl-containing polymers are employed, and it is desired to neutralize the same, this may conveniently be done without essentially interfering with water-insolubility by the employment of a long-chain fatty acid amine such as stearyl amine, stearyl dimethylamine, dimethyl hydrogenated tallow amine, or the like.

Versatyl-42™ (28-4942) (Synonym Number: 78-6342) (National Starch): Octylacrylamide/acrylates Copolymer—carboxyl-containing polymer formed from octylacrylamide and two or more monomers consisting of acrylic acid, methacrylic acid, or any of their simple esters, otherwise known as Resyn 26-4045 (National Starch) and Amphomer LV- 71™ (National Starch). Used without neutralization. Water insoluble. Alcohol soluble. Hard but flexible films. (Broader definition in U.S. Pat. No. 4,315,910)

Amphomer™ (28-4910) (National Starch): Amphoteric acrylic polymer. Relatively inflexible. Easy sprayability. Soluble in anhydrous ethanol and isopropanol. Actually: Octylacrylamide/Acrylates/Butylaminoethyl Methacrylate Copolymer resin containing carboxyl groups.

S.D. Alcohol 40: Ethyl alcohol, denatured, formula 40-2, commodity item.

Fragrance 32178: Exclusive formula like many others; composition unimportant; many fragrances are equivalent and can be employed.

Triclosan (Irgasan DP 300™—Ciba-Geigy): 2,4,4'-trichloro- 2'-hydroxydiphenylether-broad spectrum antimicrobial agent.

Steareth-2: Polyoxyethylene (2) stearyl ether (Brij 72™— ICI Americas Inc.).

Ganex V™ (GAF) Polymers: Alkylated vinyl pyrrolidone and alpha-olefin linear copolymers.

Cetyl Acetate/Acetylated Lanolin Alcohol (Acetulan™— Amerchol): Lipophilic emollient fluid (oil)—Nontacky lubricant assists in spreading.

Luviflex VMB-35™ (BASF): Copolymer of vinyl pyrrolidone, t-butyl acrylate, and methacrylic acid.

Dermacryl—79™ (National Starch): Water-insoluble acrylates/t-octylpropenamide copolymer containing carboxyl groups. Soluble in ethanol and isopropanol, may be neutralized with long-chain amines such as stearyl dimethylamine to enhance oil solubility and water-repellency. Produces relatively hard films.

Resyn 28-1310™ (National Starch): Carboxyl-containing vinyl acetate/crotonic acid copolymer, soluble in ethanol. Films are flexible and water insoluble.

Resyn 28-2913™: Carboxyl-containing vinyl acetate/crotonic acid/vinyl neodecanoate terpolymer. Especially suitable for sprays. If neutralized with long-chain amines, polymer becomes more flexible and water-insoluble.

Resyn 28-2930™ (National Starch): Same as Resyn 28-2913™ (National Starch).

Versacryl-40™ (National Starch): Carboxyl-containing octylacrylamide/acrylates copolymer.

Ucarset LP-250™ (Amerchol): Ethyl monoester of poly-(methyl-vinylether/maleic acid). Hydrophobic neutralizers such as dimethyl hydrogenated tallow amine improve hydrocarbon tolerance and water-insolubility.

Ganex™ (GAF): series of copolymers of vinyl pyrrolidone and long-chain alpha-olefins or copolymers of poly-(vinyl pyrrolidone/dimethylaminoethyl methacrylate).

Gantrez ES™ (GAF): Anionic copolymers being monoalkyl esters of poly(methyl-vinylether/maleic acid).

Stepanhold Extra™ (Stepan Company): Polyvinyl pyrrolidone/ethylmethacrylate/methacrylic acid terpolymer.

Carboset 525™ (BF Goodrich): Acrylic copolymer.

Rehydrol II™ (Reheis): Aluminum chlorohydrate composition. CTFA designation Aluminum Chlorohydrex PG. Propylene glycol composition of aluminum chlorohydrate which is soluble and stable in anhydrous alcohol.

ADVANTAGE CP™ (ISP Technologies, Inc.): Copolymer of vinyl acetate, butyl maleate, and isobornyl acrylate in ethanol; acid number 170–190; percent solids 48–52; K-value 33–39; color (VCS) two maximum, appearance at 25° C., clear to pale yellow solution in ethanol.

Carbomer 1342—Acrylic acid copolymer, carboxy polymethylene, also Carbopol 1342-carboxy vinyl polymer. A vinyl polymer with active carboxyl groups, C and E News 36, 64 (Sep. 29, 1958). From B. F. Goodrich. Another acrylic copolymer used as thickening agent.

Possible Additional Antiperspirant Active Additives

In addition to the essential ingredients of the present invention, as previously defined, may be included the usual aluminum chlorohydrate, aluminum dichlorohydrate, aluminum sesquichlorohydrate, aluminum zirconium trichlorohydrate, aluminum zirconium tetrachlorohydrate, aluminum zirconium pentachlorohydrate, aluminum zirconium octachlorohydrate, aluminum chloride, aluminum sulfate buffered, and so on, all in amounts which are now generally recognized as safe and effective or which will be, at the time of use, generally recognized as safe and effective, and in the foregoing listings of antiperspirant additives which can possibly be used, but in reduced amounts, are included the complexes with propylene glycol and polyethylene glycol as well as complexes with glycine, all as already well-known in the art and as is the subject of a monograph or directive, for example, directing that the aluminum chlorohydrate may be used at a concentration of 25% or less, and that the ratio range of aluminum to chlorine may be 2.1 down to but not including 1.9:1, all of which is so well recognized in the art as not to require further discussion here.

It is accordingly seen from the foregoing that the present invention provides a highly desirable and advantageous topical antiperspirant composition or preparation consisting essentially of an effective antiperspirant amount of a non-toxic water-insoluble occlusive film-forming antiperspirant polymer, and a method of reducing perspiration by applying such a composition to the skin of a subject in the area in which it is desired to reduce perspiration. The presence of a water-repellant or waterproofing polymer, in addition to the antiperspirant polymer, is optional but preferable and advantageous. Normally-employed mineral salts, such as aluminum and zirconium chlorohydrate, may be included in the composition but, since not essential, may be employed in reduced amounts, if present. The composition may take various usual forms, such as solutions, suspensions, or other liquid forms, dab-ons, roll-ons, or stick forms, according to the convention of the art, with stick forms being preferred from the standpoint of extended and improved effectiveness. Evaporation of non-toxic solvent, in which the polymer may be dissolved or dispersed, leaves a cosmetically-acceptable and usually clear transparent antiperspirant film which is effective for its intended purpose.

It is to be understood that the present invention is not to be limited to the exact compounds, compositions, procedures, or formulations disclosed, as numerous modifications and changes therein will immediately become apparent to one skilled in the art to which this invention pertains, wherefore the present invention is to be understood as limited only by the full scope which can be legally accorded to the appended claims.

I claim:

1. A topical antiperspirant composition consisting essentially of an effective amount of a non-toxic water-insoluble occlusive film-forming antiperspirant polymer in a topically-acceptable non-toxic medium.

2. A composition of claim 1, wherein the polymer is in solution or dispersion in said medium.

3. A composition of claim 1, wherein the medium is a non-toxic topically-acceptable medium which acts as solvent for the polymer and which evaporates after application to leave a film of the polymer.

4. A composition of claim 2, wherein the polymer is dissolved or dispersed in a non-toxic topically-acceptable alcohol or ketone.

5. A composition of claim 1, wherein the medium is selected from a lower-aliphatic alcohol and a lower-aliphatic ketone.

6. A composition of claim 5, wherein the medium is selected from the group consisting of ethyl alcohol, isopropyl alcohol, n-propanol, n-butanol, sec. butanol, isobutanol, and acetone.

7. A composition of claim 1, wherein the composition includes a topically-acceptable carrier, diluent, or excipient.

8. A composition of claim 7, wherein the composition comprises a vinyl or acrylic copolymer and is in liquid, roll-on, stick form, or dab-on form.

9. A composition of claim 1, wherein the polymer comprises an alkyl olefinic acid amide/olefinic acid or ester copolymer alone or in combination with a water-repellant polymer.

10. A composition of claim 9, wherein the polymer comprises an octylacrylamide or propenamide/acrylates copolymer alone or in combination with a water-repellant polymer.

11. A composition of claim 1, wherein the polymer comprises an alkyl olefinic acid amide/olefinic acid or ester copolymer alone or with a PVP/linear alpha-olefin copolymer.

12. A composition of claim 11, wherein the polymer comprises an octylacrylamide or propenamide/acrylates copolymer alone or with a PVP/linear alpha-olefin copolymer.

13. A composition of claim 11, wherein the polymer comprises an octylacrylamides/acrylates copolymer alone or in combination with a PVP/linear alpha-olefin copolymer.

14. A composition of claim 1, wherein the polymer comprises between about 5% and about 40% by weight.

15. A composition of claims 8 or 14, wherein the polymer comprises between about 5% and about 40% by weight, bodying agent between about 5% and about 35% by weight, emollient-plasticizer-cosolvent between about 5% and about 25% by weight, and solvent for the polymer between about 30% and about 80% by weight.

16. A composition of claim 15, wherein the polymer comprises an alkyl olefinic acid amide/olefinic acid or ester copolymer alone or with a PVP/linear alpha-olefin copolymer.

17. A composition of claim 15, wherein the polymer comprises an octylacrylamide or propenamide/acrylates copolymer alone or with a PVP/linear alpha-olefin copolymer.

18. A composition of claim 17, wherein the polymer comprises an octylacrylamides/acrylates copolymer alone or in combination with a PVP/Eicosene copolymer.

19. A composition of claim 1, wherein the polymer comprises a vinyl acetate/butyl maleate/isobornyl acrylates copolymer alone or in combination with a waterproofing agent.

20. A composition of claim 19, wherein the polymer comprises a vinyl acetate/butyl maleate/isobornyl acrylates copolymer alone or in combination with a PVP/linear alpha-olefin copolymer.

21. A composition of claim 15, wherein the polymer comprises a vinyl acetate/butyl maleate/isobornyl acrylates copolymer alone or in combination with a PVP/Eicosene copolymer.

22. A method of topically reducing perspiration in a subject consisting essentially of the step of topically applying to the skin of the subject in the area in which it is desired to reduce perspiration a topical antiperspirant composition consisting essentially of an effective amount of a non-toxic water-insoluble occlusive film-forming antiperspirant polymer in a topically-acceptable non-toxic medium.

23. A method of claim 22, wherein the composition applied to the skin of the subject comprises the polymer plus a non-toxic topically-acceptable medium which acts as solvent for the polymer and wherein after application the solvent is evaporated to leave a film of the polymer.

24. A method of claim 22, wherein the polymer is in solution or dispersion in said medium.

25. A method of claim 22, wherein the medium is a non-toxic topically-acceptable medium which acts as solvent for the polymer and which evaporates after application to leave a film of the polymer.

26. A method of claim 24, wherein the polymer is dissolved or dispersed in a non-toxic topically-acceptable alcohol or ketone.

27. A method of claim 22, wherein the medium is selected from a lower-aliphatic alcohol and a lower-aliphatic ketone.

28. A method of claim 27, wherein the medium is selected from the group consisting of ethyl alcohol, isopropyl alcohol, n-propanol, n-butanol, sec. butanol, isobutanol, and acetone.

29. A method of claim 22, wherein the composition includes a topically-acceptable carrier, diluent, or excipient.

30. A method of claim 29, wherein the composition comprises a vinyl or acrylic copolymer and is in liquid, roll-on, stick form, or dab-on form.

31. A method of claim 22, wherein the polymer comprises an alkyl olefinic acid amide/olefinic acid or ester copolymer alone or in combination with a water-repellant polymer.

32. A method of claim 31, wherein the polymer comprises an octylacrylamide or propenamide/acrylates copolymer alone or in combination with a water-repellant polymer.

33. A method of claim 22, wherein the polymer comprises an alkyl olefinic acid amide/olefinic acid or ester copolymer alone or with a PVP/linear alpha-olefin copolymer.

34. A method of claim 33, wherein the polymer comprises an octylacrylamide or propenamide/acrylates copolymer alone or with a PVP/linear alpha-olefin copolymer.

35. A method of claim 33, wherein the polymer comprises an octylacrylamides/acrylates copolymer alone or in combination with a PVP/linear alpha-olefin copolymer.

36. A method of claim 22, wherein the polymer comprises between about 5% and about 40% by weight.

37. A method of claim 29 or 36, wherein the polymer comprises between about 5% and about 40% by weight, bodying agent between about 5% and about 35% by weight, emollient-plasticizer-cosolvent between about 5% and about 25% by weight, and solvent for the polymer between about 30% and about 80% by weight.

38. A method of claim 37, wherein the polymer comprises an alkyl olefinic acid amide/olefinic acid or ester copolymer alone or with a PVP/linear alpha-olefin copolymer.

39. A method of claim 37, wherein the polymer comprises an octylacrylamide or propenamide/acrylates copolymer alone or with a PVP/linear alpha-olefin copolymer.

40. A method of claim 39, wherein the polymer comprises an octylacrylamides/acrylates copolymer alone or in combination with a PVP/Eicosene copolymer.

41. A method of claim 22, wherein the polymer comprises a vinyl acetate/butyl maleate/isobornyl acrylates copolymer alone or in combination with a waterproofing agent.

42. A method of claim 41, wherein the polymer comprises a vinyl acetate/butyl maleate/isobornyl acrylates copolymer alone or in combination with a PVP/linear alpha-olefin copolymer.

43. A method of claim 37, wherein the polymer comprises a vinyl acetate/butyl maleate/isobornyl acrylates copolymer alone or in combination with a PVP/Eicosene copolymer.

\* \* \* \* \*

UNITED STATES PATENT AND TRADEMARK OFFICE
CERTIFICATE OF CORRECTION

PATENT NO. : 5,508,024
DATED : April 16, 1996
INVENTOR(S) : Frank Tranner

It is certified that error appears in the above-indentified patent and that said Letters Patent is hereby corrected as shown below:

Column 12, line 45: Please insert -- OVERVIEW OF ANTIPERSPIRANT/DEODORANT STICK OF THE PRESENT INVENTION

Polymer Antiperspirant/Deodorant Stick
Non-Aluminum/Zirconium Chlorohydrate Product Rationale General Description:
A creamy-white solid with a firm consistency and packaged in an oval "propel/repel" container with a surface seal.

General Function and Purpose:
To impart to the underarms a film which:
a. reduces perspiration,
b. helps prevent perspiration odor,
c. and produces a pleasant fragrance. --.

UNITED STATES PATENT AND TRADEMARK OFFICE
CERTIFICATE OF CORRECTION

PATENT NO. : 5,508,024
DATED : April 16, 1996
INVENTOR(S) : Frank Tranner

It is certified that error appears in the above-indentified patent and that said Letters Patent is hereby corrected as shown below:

Column 15, line 48: Insert -- Antiperspirant Study #999-064 --.

Signed and Sealed this

Fifteenth Day of October, 1996

Attest:

BRUCE LEHMAN

Attesting Officer

Commissioner of Patents and Trademarks